United States Patent [19]

Dogru et al.

[11] Patent Number: 4,868,751
[45] Date of Patent: Sep. 19, 1989

[54] METHOD FOR DETERMINING RELATIVE PERMEABILITY OF A SUBTERRANEAN RESERVOIR

[75] Inventors: Ali H. Dogru, Dallas; Eve S. Sprunt, Farmers Branch, both of Tex.

[73] Assignee: Mobil Oil Corporation, New York, N.Y.

[21] Appl. No.: 95,210

[22] Filed: Sep. 11, 1987

[51] Int. Cl.$^4$ .......................................... G01N 15/08
[52] U.S. Cl. ........................................ 364/422; 73/38
[58] Field of Search ................... 364/422, 556, 420; 73/38

[56] References Cited

U.S. PATENT DOCUMENTS

| 3,839,899 | 10/1974 | McMillen | 73/38 |
|---|---|---|---|
| 4,283,629 | 8/1981 | Habermehl et al. | 250/445 |
| 4,422,177 | 12/1983 | Mastronardi et al. | 378/17 |
| 4,487,056 | 12/1984 | Wiley | 73/38 |
| 4,543,821 | 10/1985 | Davis | 73/38 |
| 4,622,643 | 11/1986 | Dotson | 73/38 |
| 4,638,447 | 1/1987 | Odeh | 73/38 |
| 4,649,483 | 3/1987 | Dixon, Jr. | 364/422 |
| 4,669,299 | 6/1987 | Closmann | 73/38 |
| 4,672,840 | 6/1987 | Cullick | 73/38 |
| 4,688,238 | 8/1987 | Sprunt et al. | 378/4 |

OTHER PUBLICATIONS

"API Recommended Practice for Core-Analysis Procedure", *Am. Petroleum Inst.*, Dalla First Edition, 8/60, pp. 2–55.

*Primary Examiner*—Jerry Smith
*Assistant Examiner*—Gail O. Hayes
*Attorney, Agent, or Firm*—Alexander J. McKillop; Charles J. Speciale; George W. Hager, Jr.

[57] ABSTRACT

A core sample from a subterranean reservoir is placed in a pressure cell holder and the core pressure is measured at a plurality of pressure points along the core before and during fluid flooding. A computed tomography (CT) scanning system provides images of the density distribution within the core sample during such waterflooding. Fluid saturation, determined from these CT images, and pressure gradients, determined from the pressure measurements are used to determine the relative permeability of the subterranean reservoir.

2 Claims, 3 Drawing Sheets

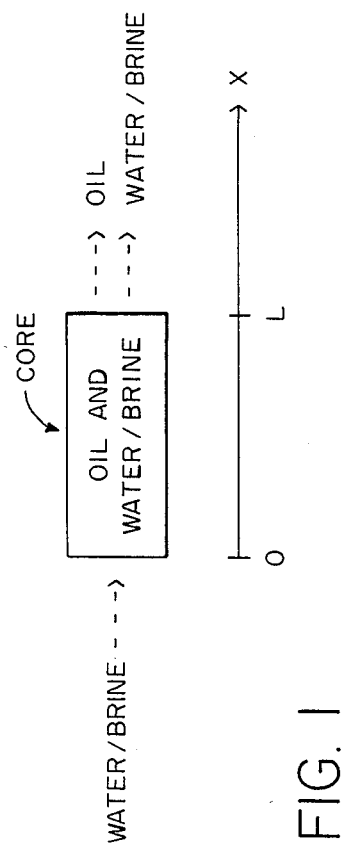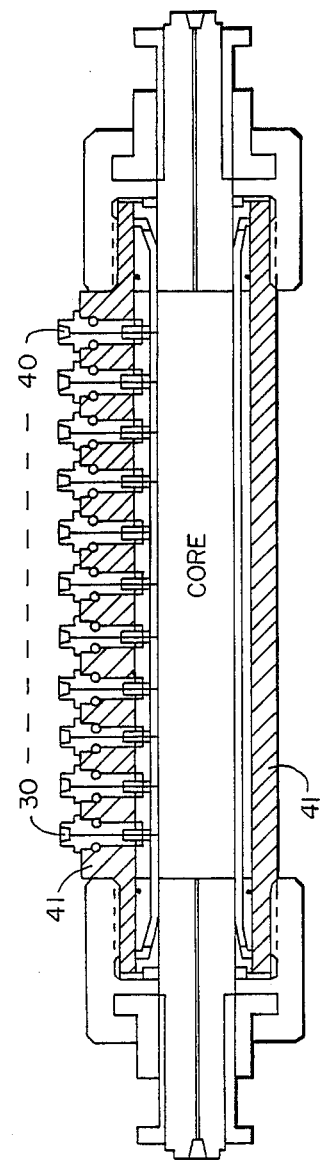

METHOD FOR DETERMINING RELATIVE PERMEABILITY OF A SUBTERRANEAN RESERVOIR

BACKGROUND OF THE INVENTION

In the production of minerals, e.g., oil and gas, certain properties of a subterranean reservoir must be determined. One of the most important of these properties is the permeability of the reservoir. Permeability of a material is a measure of the ability of the material to transmit fluids through its pore spaces and is inversely proportional to the flow resistance offered by the material. Normally, permeability is determined by taking core samples from the reservoir and carrying out well-defined measurement techniques on the samples. There are several techniques available for making such measurements, many of which are described in *PETROLEUM PRODUCTION ENGINEERING—DEVELOPMENT* by L. C. Uren, Fourth Edition, McGraw-Hill Book Company, Inc., 1956, pps. 660-669. Another standard reference is American Petroleum Institute, *API RECOMMENDED PRACTICE FOR CORE-ANALYSIS PROCEDURE, API RP40*, 1960.

More particularly, the relative permeability plays a very important role in describing the fluid flow in oil and gas reservoirs. Two methods of measurement are practiced by the industry, steady-state and dynamic displacement. In each method a cylindrical core is saturated with water or brine, then oil flooded to irreducible water saturation. Subsequently the core is waterflooded or brine flooded and the pressure drop across the core is measured along with the oil and water or brine production. The average saturations within the core are determined from the overall material balance. The steady-state method requires lengthy measurement times because it requires stabilization of the fluid flow. The dynamic displacement method overcomes this, however, it suffers from capillary and effects. Hence the displacement method is only effective for high flow rates.

It is therefore an object of the present invention to provide a new and improved method for determining the relative permeability of a subterranean reservoir by way of selective measurements on a core sample from such reservoir.

SUMMARY OF THE INVENTION

The present invention is related to a method for determining relative permeability of a subterranean reservoir. A core sample is taken from such reservoir. Both pressure and fluid saturation are measured at a plurality of corresponding positions along the core before and during fluid flooding of the core. From these pressure and saturation measurements the relative permeability of the reservoir is determined.

More particularly, an initial saturation fluid relative permeability is determined from the taking of core measurements of (i) the initial fluid saturation condition prior to flooding with a displaying fluid, (ii) the pressure gradient along the core, (iii) the displaying fluid injection rate, (iv) the production rates of both the initial saturation fluid and the displacing fluid, and (v) the change in initial fluid saturation. The displacing fluid relative permeability is determined from the taking of the same core measurements with the additional taking of core measurements of the change in displacing fluid saturation and the displacing fluid saturation gradient.

BRIEF DESCRIPTION OF THE DRAWINGS

FIG. 1 is a graphical representation of fluid flow through a core sample in accordance with the method of the present invention.

FIG. 2 is a cross-sectional view of a multi-tap pressure core holder for use in carrying out pressure measurements in accordance with the method of the present invention.

DESCRIPTION OF THE PREFERRED EMBODIMENTS

Figure 3:
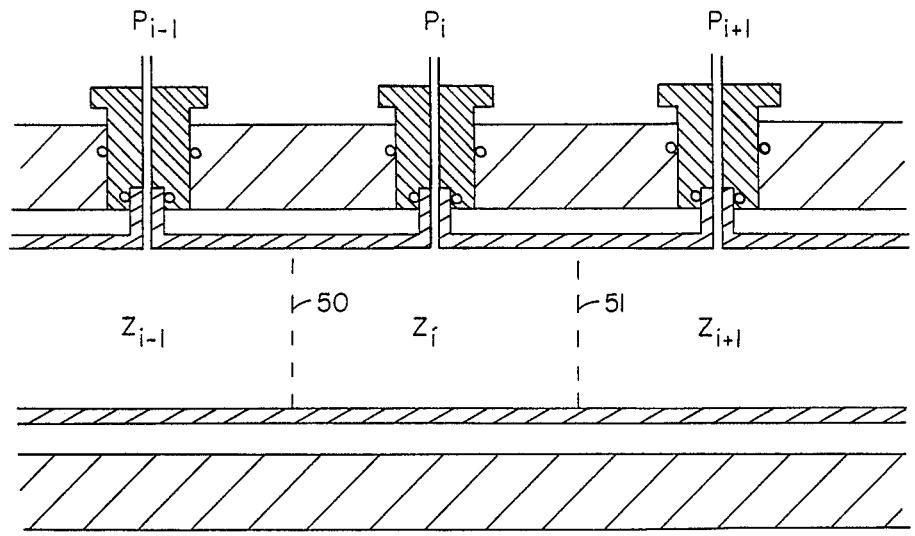
FIGS. 3 and 4 illustrate alternate embodiments for carrying out the pressure measurements with the pressure core holder of FIG. 2.

In accordance with the present invention, local pressure gradients and fluid saturations are measured on a core sample taken from a subterranean reservoir. From these measurements the relative permeability is determined. Core end effects are eliminated by measuring the pressure and saturation at points along the length of the core that are located away from the effluent boundary of the core. In this manner of taking the measurements, the capillary pressure between the fluids in the core (i.e. oil, water or brine) can be considered negligible for a linear, horizontal system.

At the start of the relative permeability measurement, the core is fully saturated with a known weight or volume of saturating fluid, such as an oil or a brine. Dual-energy X-ray CT scans are retaken at a plurality of scan positions. Thereafter, the core saturation is altered by flowing a displacing fluid, such as oil, water or brine, other than that with which the core is saturated, through the core and both saturation and pressure measurements made.

Before describing a method and apparatus for carrying out such saturation and pressure measurements, reference is first made to FIG. 1 along with the following description of the fluid flow conditions through the core sample of FIG. 1 during the flooding of a core sample to displace the initial saturation fluids.

FIG. 1 graphically depicts the fluid flow during the waterflooding of a core of length L from a subterranean reservoir containing both oil and water. Hereinafter, the terms water and waterflooding are intended to include brine and brine flooding respectively. Both the oil and water are considered to homogeneous and incompressible fluids with constant viscosities under laboratory conditions. The differential equations describing the oil and water flow are:

$$\frac{\partial}{\partial x}\left(k\frac{k_{ro}}{\mu_o}\frac{\partial P}{\partial x}\right) + q_o(L,t) = \phi\frac{\partial S_o}{\partial t} \quad (1)$$

$$\frac{\partial}{\partial x}\left(k\frac{k_{rw}}{\mu_w}\frac{\partial P}{\partial x}\right) + q_w(x,t) = \phi\frac{\partial S_W}{\partial t} \quad (2)$$

-continued $$S_o + S_W = 1 \tag{3}$$

The initial and boundary conditions are:

$$P(x,0) = P_i \text{ for } 0 < x < L \tag{4}$$

$$S_W(x,0) = S_{Wi} \text{ for } 0 < x < L \tag{5}$$

$$S_o(x,0) = S_{oi} \text{ for } 0 < x < L \tag{6}$$

$$q_o(x,0) = 0 \text{ for } 0 < x < L \tag{7}$$

$$q_W(x,0) = 0 \text{ for } 0 < x < L \tag{8}$$

$$q_W(0,t) = q_{W,\text{inj}} \text{ for } 0 < t < T \tag{9}$$

$$q_W(L,t) = q_W(t) \text{ measured } 0 < t < T \tag{10}$$

$$q_o(L,t) = q_o(t) \text{ measured } 0 < t < T \tag{11}$$

$$\frac{\partial P}{\partial x}(0,t) = \frac{\partial P}{\partial L}(L,t) = 0 \tag{12}$$

From these equations, an oil relative permeability curve will firstly be determined. Carrying out the differentation in the oil equation (1) with respect to distance X yields:

$$\frac{k}{\mu_o}\left(\frac{\partial k_{ro}}{\partial x}\frac{\partial P}{\partial x} + k_{ro}\frac{\partial^2 p}{\partial x^2}\right) + q_o(L,t) = \phi\frac{\partial S_o}{\partial t} \tag{13}$$

Rearranging equation (13) yields:

$$\left(\frac{\partial P}{\partial x}\right)\frac{\partial k_{ro}}{\partial x} + \left(\frac{\partial^2 p}{\partial x^2}\right)k_{ro} = \frac{\mu_o}{k}\phi\frac{\partial S_o}{\partial t} - \frac{\mu_o}{k}q_o(L,t) \tag{14}$$

Since:

$$\frac{\partial k_{ro}}{\partial x} = \frac{\partial k_{ro}}{\partial S_o}\frac{\partial S_o}{\partial x} \tag{15}$$

Equation (14) becomes:

$$\left[\left(\frac{\partial P}{\partial x}\right)\left(\frac{\partial S_o}{\partial x}\right)\right]\frac{dk_{ro}}{dS_o} + \left[\frac{\partial^2 P}{\partial x^2}\right]k_{ro} = \frac{\phi\mu_o}{k}\frac{\partial S_o}{\partial t} - \frac{\mu_o}{k}q_o(L,t) \tag{16}$$

Dividing each side of equation (16) by $$(\partial P/\partial x)(\partial S_o/\partial x) \text{ yields:}$$

$$\frac{dk_{ro}}{dS_o} + A_o(x,t) k_{ro} = B_o(x,t) \tag{17}$$

$$k_{ro}(S_{or}) = 0 \tag{18}$$

Equation (17) is a first-order, ordinary differential equation in terms of $k_{ro}$. The coefficients $A_o$ and $B_o$ are given by:

$$A_o(x,t) = \frac{\frac{\partial^2 p}{\partial x^2}}{\frac{\partial P}{\partial x}\frac{\partial S_o}{\partial x}} \tag{19}$$

$$B_o(x,t) = \frac{\frac{\mu_o}{k}\left(\phi\frac{\partial S_o}{\partial t} - q_o(L,t)\right)}{\frac{\partial P}{\partial x}\frac{\partial S_o}{\partial x}} \tag{20}$$

If the coefficients $A_o$ and $B_o$ are determined from measurements at locations x and at time t, equation (17) can be integrated analytically or numerically to determine a relative oil permeability curve $k_{ro}(S_o)$ for the measured range of $S_o$ in the core. For example, if the core contains oil saturations from the irreducible to the initial, at time t, solution of equation (17) will determine a complete relative oil permeability curve at one time step.

Measurements required for the foregoing include the following:
 (i) oil saturation inside the core, $S_o(x,t)$,
 (ii) pressure gradients inside the core, $(\partial P/\partial x)(x,t)$,
 (iii) water injection rate, $q_w(o,t)$,
 (iv) water production rate, $q_w(L,t)$,
 (v) oil production rate, $q_o(L,t)$, and
 (vi) change in oil saturation at location x and time t, $(\partial S_o/\partial t)(x,t)$.

Secondly, a water relative permeability curve will be determined in similar manner to that for the oil relative permeability curve. Differentiating the water equation (2) with respect to distance x and operating on such differentiation in the same manner as set forth in equations (13)–(16) yields:

$$\frac{dk_{rw}}{dS_w} + A_w(x,t) k_{rw} = B_w(x,t) \tag{21}$$

$$k_{rw}(S_{wi}) = 1, \tag{22}$$

$$A_w(x,t) = \frac{\frac{\partial^2 p}{\partial x^2}}{\frac{\partial P}{\partial x}\frac{\partial S_W}{\partial x}} \tag{23}$$

$$B_w(x,t) = \frac{\frac{\mu_W}{k}\left[\phi\frac{\partial S_W}{\partial t} - q_W(x,t)\right]}{\frac{\partial P}{\partial x}\frac{\partial S_W}{\partial x}} \tag{24}$$

If the coefficients $A_w$ and $B_w$ are determined from measurements at location X and at time t, equation (21) can be integrated analytically or numerically to determine a relative water permeability curve $k_{rw}(S_w)$ for the measured range of $S_w$ in the core. For example, if the core contains water saturations from the irreducible to the initial, at time t, solution of equation (21) will determine a complete relative water permeability curve at one time step.

Measurements required in addition to (i)–(vi) set forth above include the following:
 (vii) change in water saturation at location x for time t, $\partial S_w/\partial t$, and
 (viii) water saturation gradient at location x for time t, $\partial S_w/\partial x$.

The following nomenclature has been utilized for the foregoing equations (1)–(24):

k = absolute permeability, Darcy,
L = total length of the core, centimeters (cm),
P = fluid pressure, Atmospheres,
$P_i$ = initial fluid pressure, Atmospheres,
q = production or injection rate, cm³/sec,
$q_w$,inj = water injection rate, cm³/sec,
$q_o(t)$ = oil production rate measured at time t, cm³/sec,
$q_w(t)$ = water production rate measured at time t, cm³/sec,
$S_o$ = oil saturation, fraction of pore volume,
$S_{oi}$ = initial oil saturation, fraction of pore volume,
$S_w$ = water saturation, fraction of pore volume,
$S_{wi}$ = initial water saturation, fraction of pore volume,
t = time, sec,
T = total test time, sec,
x = space coordinate, cm,
θ = porosity of the rock, fraction,
$\mu_o$ = oil viscosity, centipoise (cp),
$\mu_w$ = water viscosity, centipoise (cp).

Having described above in detail the measurements needed for determining relative permeability in accordance with the present invention, there will now be describd a preferred method for carrying out such measurements as well as the apparatus to be utilized. The pressure measurement will be described followed by a description of the saturation measurement. Both measurements are made locally within a core sample.

Pressure is measured at a plurality of locations along a core sample from the reservoir using a multi-tap pressure core holder as shown in FIG. 2. The pressure taps, such as those at locations 30 through 40 are connected to pressure transducers or pressure gages so that the changes in pressure along the length of the core sample can be determined. If the hydrocarbon saturation is to be determined by an X-ray technique such as CT scanning the multitap core holder body 41 should be constructed of a low density material such as an aluminum alloy, a titanium alloy or lucite. If the hydrocarbon saturation is to be determined with a nuclear magnetic resonance (NMR) technique the multitap core holder body 41 should be constructed of non-magnetic material.

Figure 4:
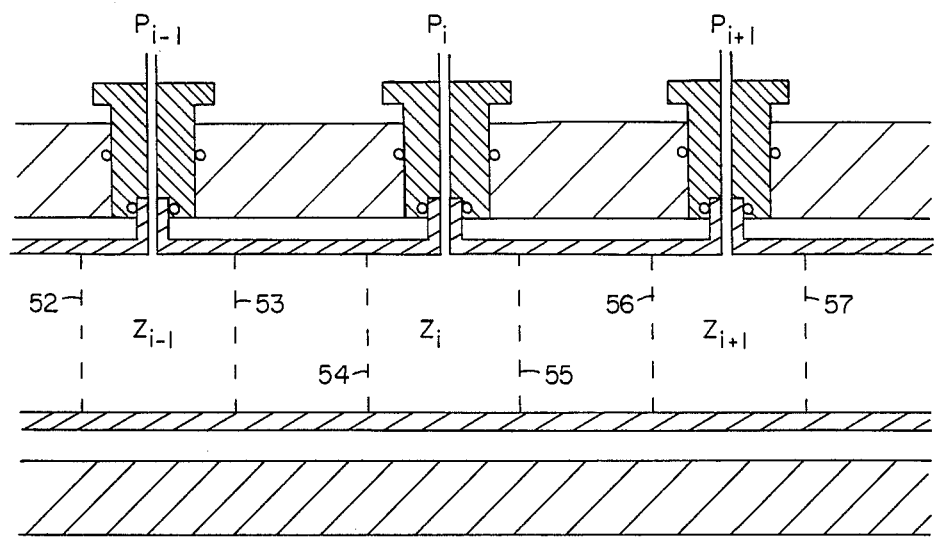

FIGS. 3 and 4 illustrate in more detail alternate embodiments for the taking of the saturation measurements. In FIG. 3 the core is divided into zones $Z_{i-1}$, $Z_i$, and $Z_{i+1}$, saturation is determined by the taking of the CT scan slices mid way between each of the pressure taps as illustrated by the dashed lines 50 and 51. The pressure measured at the ith pressure tap is, for example, Pi. This pressure Pi is associated with the saturation Si measured in zone Zi. In FIG. 4 the core is divided into zones $Z_{i-1}$, Zi, and $Z_{i+1}$ which cover only a portion of the core between pressure tapes, saturation is determined by the taking of CT scan slices as illustrated by the dashed lines 52–57.

Figure 5:
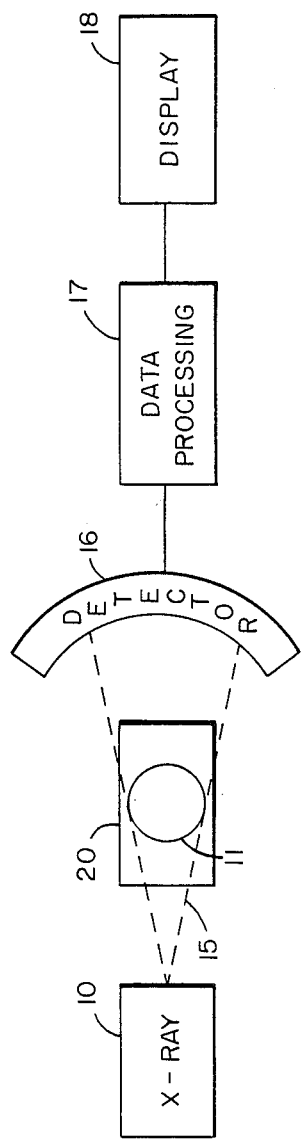
FIG. 5 illustrates a computed tomography system for use in carrying out saturation measurements in accordance with the method of the present invention.

Secondly, saturation may be measured using x-ray attenuation. In one embodiment the computed tomography (CT) scanning system of FIG. 5 may be utilized. This CT scanning system produces a display or image of the density distribution in a cross-section or transverse slice of the core. X-ray energy provided by the X-ray tube 10 passes through the core sample 11 and falls on the detector array 16. Rotation and indexing of core sample 11 within the X-ray fan beam 15 is provided by the gantry 20. After a desired number of scans are completed for each sample slice, the core is indexed to place the next sample slice within the path of the X-ray fan beam 15. Signals from detector 16 are applied through data processing unit 17 to display 18 where the CT images are viewed. While not forming a part of the present invention, such a CT scanning system is used in accordance with the method of the present invention to determine saturation of the pore spaces within the core sample. For a more detailed description of CT scanning systems which reference may be made to U.S. Pat. Nos. 4,649,483 to Dixon, Jr.; 4,157,472 to Beck, Jr. and Barrett; 4,399,509 to Hounsfield; 4,283,629 to Habermehl; and 4,422,177 to Mastronardi et al; and to an article entitled "Computed Tomographic Analysis of Meteorite Inclusions", Science, pages 383–384, Jan. 28, 1983, the teachings of which are incorporated herein by reference. The CT scanning system of the aforementioned patent to Dixon, Jr. is particularly applicable to the method of the present invention in that Dixon Jr. describes in detail the steps of determining the multi-phase fluid saturation of a core sample from a subterranean reservoir utilizing X-ray mass attenuation coefficients for the core sample obtained from the plurality of X-ray images. From these X-ray mass attenuation coefficients, the weight fractions and volume fractions of each phase of the fluid is determined.

Figure 6:
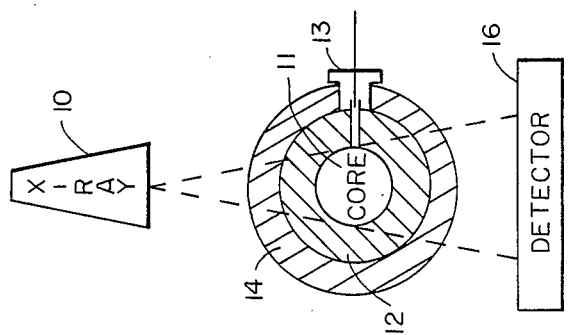
FIG. 6 is a cross-sectional simplified view of the orientation of a core mounted in the pressure holder of FIG. 2 and subjected to x-ray scanning by the computed tomography system of FIG. 3.

In using the system and method described in Dixon, Jr., the orientation of the CT system with respect to the core pressure holder is shown in FIG. 6. Core 11, surrounded by the molded core sleeve 12 is mounted within the multi-tap pressure core holder 14. In such FIG. 6 the multi-tap core holder 14 is shown in a simplified cross-sectional pictorial view with a single pressure tap 13 leading to the core 11. The CT scans are positioned on either side of the pressure taps, such as pressure tap 13. The X-ray slice that the CT scan makes through the core 11 should be at least one half a CT scan slice width away from the edge of the pressure tap to avoid artifacts. For example, if the slice width is 3 millimeters, the CT scan slice should be 1.5 millimeters from the edge of the pressure tap. Reference X-ray CT scans are obtained at known end point saturations on either side of each of the plurality of pressure taps at two or more X-ray energies for each scan position to allow dual-energy scanning. Such reference end point saturation conditions include oven dry, fully water saturated and fully oil saturated. The average intensity of the resulting CT images establish the CT numbers for the core sample fluids. These CT numbers are utilized in accordance with the teaching of the aforementioned U.S. patent to Dixon, Jr. to determine the saturation for each CT scan slice.

If it is important to maintain the original wettability of the core, the oven-dry reference CT scans may be obtained last. In this event, the saturation data would be obtained before the core is cleaned and dried.

The foregoing described method of the present invention has involved the displacing of an initial saturating fluid within a core sample by the flood of such core sample with a different saturation agent or fluid and the determination of relative permeabilities through saturation and pressure measurements carried out during the flooding of the core sample with the displacing fluid.

This method is sometimes expanded in actual practice. For example, in one embodiment, a core sample is saturated with water or brine, then oil-flooded to irreducible water saturation and subsequently water or brine flooded. The core sample may then be oil flooded again. Several relative permeability measurements involving oil displacing water or brine and water or brine displacing oil may be carried out.

Having now described preferred methods for obtaining both pressure and saturation information, it will be apparent to those skilled in the art that various methods may be employed to obtain such information since such methods do not form part of the present invention. For example, differing configurations of a pressure core holder may be employed in making the pressure measurements. Also, other saturation determination techniques such as digital projection X-ray imaging, as in a fluoroscope, may be utilized. Even further, fluid saturation may be determined inside a non-metallic test cell using a nuclear magnetic resonance (NMR) device. It is the combined use of the pressure and saturation measurements, however obtained, to determine core permeability in accordance with the algorithms set forth hereinabove that constitutes the present invention as now set forth in the appended claims.

We claim:

1. Method for determining relative permeability of a subterranean reservoir, comprising the steps of:
    (a) measuring a first fluid saturation inside a core sample from said subterranean formation,
    (b) flooding said core sample with a second fluid to displace said first fluid from within said core sample,
    (c) measuring pressure gradients along the core during said flooding,
    (d) measuring the second fluid injection rate during said flooding,
    (e) measuring the second fluid production rate during said flooding,
    (f) measuring the first fluid production rate during said flooding,
    (g) measuring the change in the first fluid saturation inside said core sample following flooding of said core sample with said second fluid,
    (h) measuring the change in the second fluid saturation inside the core following said flooding with said second fluid,
    (i) measuring the second fluid saturation gradients along said core following said flooding with said second fluid, and
    (j) determining the relative permeability of said core sample from the saturation and pressure measurements taken at the same positions along said core sample as well as said fluid injection and production rates.

2. Method for determining relative permeability of a core sample from a subterranean reservoir, comprising the steps of:
    (a) measuring the fluid saturation $S_o(x,t)$ inside the core,
    (b) measuring the pressure gradients $(\partial P/\partial x)(x,t)$ along said core,
    (c) flooding said core with a displacing fluid,
    (d) measuring the displacing fluid injection rate $q_w(o,t)$,
    (e) measuring the displacing fluid production rate $q_w(L,t)$,
    (f) measuring the initial saturation fluid production rate $q_o(L,t)$,
    (g) measuring the change in fluid saturation $(\partial S_o/\partial t)(x,t)$,
    (h) measuring the change in displacing fluid saturation $\partial S_w/\partial t$,
    (i) measuring the displacing fluid saturation gradient $\partial S_w/\partial w$ along said core,
    (j) determining the relative initial saturation fluid permeability from the following expressions:

$$dk_{ro}/dS_o + A_o(x,t)k_{ro} = B_o(x,t), \text{ and}$$

$$k_{ro}(S_{oi}) = 0, \text{ where}$$

$$A_o(x,t) = (\partial^2 p/\partial x^2)/[(\partial P/\partial x)(\partial S_o/\partial x)], \text{ and}$$

$$B_o(x,t) = (\mu_o/k)[\phi \partial S_o/\partial t - q_o(L,t)]$$

$$/[(\partial P/\partial x)(\partial S_o/\partial x)], \text{ and}$$

(k) determining the relative displacing fluid permeability from the following expressions:

$$(dk_{rW}/dS_W) + A_W(x,t)k_{rW} = B_W(x,t) \text{ and}$$

$$k_{rW}(S_{Wi}) = 1, \text{ where}$$

$$A_W(x,t) = (\partial^2 P/\partial x^2)/[(\partial P/\partial x)(\partial S_W/\partial x)], \text{ and}$$

$$B_W(x,t) = (\mu_o/k)[\phi \partial S_W/\partial t - q_W(x,t)]$$

$$/(\partial P/\partial x)(\partial S_W/\partial x),$$

wherein the following nomenclature is utilized in the above identified steps:

k = absolute permeability, Darcy,
L = total length of the core, centimeters (cm),
P = fluid pressure, Atmospheres,
$P_i$ = initial fluid pressure, Atmospheres,
q = production or injection rate, cm³/sec,
$q_{w,inj}$ = displacing fluid injection rate, cm³/sec,
$q_o(t)$ = initial saturation fluid production rate measured at time t, cm³/sec,
$q_w(t)$ = displacing fluid production rate measured at time t, cm³/sec,
$S_o$ = fluid saturation, fraction of pore volume,
$S_{oi}$ = initial fluid saturation, fraction of pore volume,
$S_w$ = displacing fluid saturation, fraction of pore volume,
$S_{wi}$ = initial displacing fluid saturation, fraction of pore volume,
t = time, sec,
T = total test time, sec,
x = space coordinate, cm,
$\theta$ = porosity of the rock, fraction,
$\mu_o$ = initial saturation fluid viscosity, centipoise (cp), and
$\mu_w$ = displacing fluid viscosity, centipoise (cp).

* * * * *